United States Patent
Kim (10) Patent No.: US 9,907,899 B2
(45) Date of Patent: Mar. 6, 2018

(54) DEVICE AND METHOD OF EXTRACTING HIGH-CONCENTRATION PLASMA FROM WHOLE BLOOD

(71) Applicant: Hong Kim, Asan-si (KR)

(72) Inventor: Hong Kim, Asan-si (KR)

( * ) Notice: Subject to any disclaimer, the term of this patent is extended or adjusted under 35 U.S.C. 154(b) by 673 days.

(21) Appl. No.: 14/137,161

(22) Filed: Dec. 20, 2013

(65) Prior Publication Data

US 2015/0101995 A1   Apr. 16, 2015

(30) Foreign Application Priority Data

Oct. 15, 2013 (KR) .................. 10-2013-0122896

(51) Int. Cl.
*A61M 1/34* (2006.01)
*G01N 33/49* (2006.01)
*B01D 63/02* (2006.01)
*B01D 63/08* (2006.01)

(52) U.S. Cl.
CPC ......... *A61M 1/3496* (2013.01); *G01N 33/491* (2013.01); *B01D 63/02* (2013.01); *B01D 63/08* (2013.01); *B01D 2311/2676* (2013.01)

(58) Field of Classification Search
CPC ...... A61M 1/3496; A61M 1/382; A61M 1/34; A61M 1/3693; A61M 1/029; A61M 5/19; A61B 5/150755; G01N 33/491; B01D 61/18; B01D 61/145; B01D 61/243; B01D 63/02; B01D 63/08; B01D 2311/2676

See application file for complete search history.

(56) References Cited

U.S. PATENT DOCUMENTS

| | | | | |
|---|---|---|---|---|
| 3,228,876 A * | 1/1966 | Mahon | ...................... | A23F 5/28 127/40 |
| 5,674,394 A * | 10/1997 | Whitmore | ........... | A61M 1/3496 210/321.6 |
| 6,010,627 A * | 1/2000 | Hood, III | ............... | A61K 35/14 210/321.6 |
| 2005/0205498 A1* | 9/2005 | Sowemimo-Coker | . | A61K 35/15 210/782 |

(Continued)

FOREIGN PATENT DOCUMENTS

KR   10-2010-0041436 A   4/2010
KR   10-2010-0116106 A   10/2010

*Primary Examiner* — David C Mellon
(74) *Attorney, Agent, or Firm* — Novick, Kim & Lee, PLLC; Jae Youn Kim (57) ABSTRACT

Disclosed are a device and method of extracting high-concentration plasma from whole blood. The device comprises: a first syringe; a centrifugation tube that is connected to the first syringe in order to centrifuge whole blood received in the first syringe; a cap that is connected to the first syringe in order to re-centrifuge plasma collected in the first syringe by centrifugation of the whole blood; and a membrane filter comprising: a body that is cylindrical in shape and has a pair of spaced inlets to which the first syringe and a second syringe are to be respectively connected; a hollow membrane included in the body; and a first space formed between the body and the membrane and serving to collect components that passed through the membrane. According to the invention, high-concentration plasma containing a high concentration platelet is obtained without having to use a kit.

5 Claims, 9 Drawing Sheets

(56) References Cited

U.S. PATENT DOCUMENTS

| | | | |
|---|---|---|---|
| 2009/0020696 A1* | 1/2009 | Bier | G01N 35/1095 250/288 |
| 2014/0110317 A1* | 4/2014 | Hoyt | A61M 1/0272 210/91 |

* cited by examiner

FIG. 1

PRIOR ART

DEVICE AND METHOD OF EXTRACTING HIGH-CONCENTRATION PLASMA FROM WHOLE BLOOD

BACKGROUND OF THE INVENTION

Field of the Invention

The present invention relates to the extraction of high-concentration plasma from whole blood, and more particularly to a device and method of extracting high-concentration plasma from whole blood by passing plasma, separated and collected from whole blood, through a membrane filter.

Description of the Prior Art

Generally, whole blood is largely divided into blood corpuscles and plasma. Herein, the blood corpuscles include red blood cells, white blood cells and platelets, and the plasma includes mainly water and contains blood coagulation factors and electrolytes.

More specifically, plasma has a water content of 91%, a protein content of 7%, a fat content of 1% and an inorganic ion content of 0.9%. Herein, the protein in plasma can be separated into albumin and globulin using the difference in solubility in ammonium sulfate and consists of a mixture of several proteins. Albumin accounts for about 55% of plasma protein and plays an important role in the supply of protein and the maintenance of colloidal osmotic pressure. Further, globulin accounts for about 38% of plasma protein and can be classified into three kinds: α, β and γ globulins. α-globulin contains lipoprotein and glycoprotein and is used to deliver vitamins and hormones, and β-globulin is used to deliver prothrombin, plasma thromboplastin, iron and copper, and γ-globulin mainly contains immune antibodies.

Plasma that plays an important role in blood as described above can supply nutrients to the human body while inhibiting harmful substances.

Figure 1:
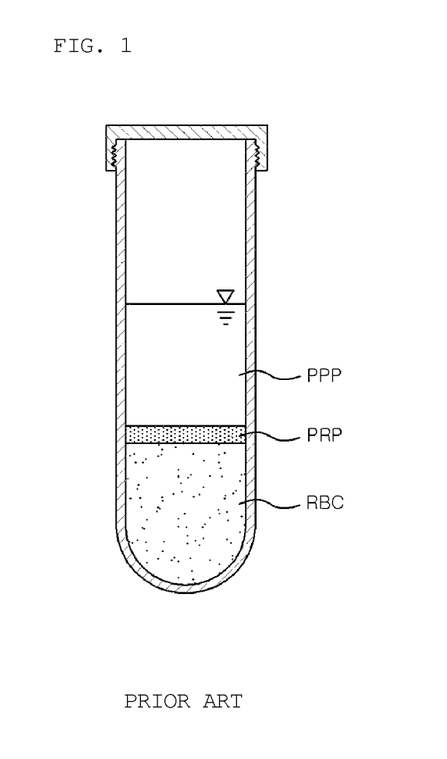
FIG. 1 is a side view showing centrifuged whole blood.

As shown in FIG. 1, whole blood (Wb) is centrifuged into a red blood cell (RBC) layer, a platelet-rich plasma (PRP) layer and a platelet-poor plasma (PPP) layer, and the platelet-rich plasma (PRP) and the platelet-poor plasma (PPP) are collected. For example, about 2.5 ml of platelet-rich plasma (PRP) and about 2.5 ml of platelet-poor plasma (PPP) can be obtained from 10 ml of whole blood. Herein, platelet-rich plasma (PRP) has been used in various treatment and beauty fields, including wound healing in implant placement including sinus elevation, heart surgery, plastic operation, dermatology and the like. Plate-poor plasma (PPP), separated and collected from whole blood (Wb), contains small amounts of platelet and protein. This platelet-poor plasma (PPP) is used as a massage material after platelet-poor plasma (PRP) therapy or is disposed of as waste. In addition, platelet-rich plasma (PRP) prepared by conventional methods contains a high concentration of platelet, but has a shortcoming in that the concentration of plasma therein is only two times higher than that in whole blood. Thus, there is a need to concentrate plasma in addition to platelet, except for red blood cells among the components of whole blood. For this purpose, in the prior art, a method of either extracting plasma from platelet-poor plasma (PPP) by a filtration process or concentrating only plasma by a concentration process was used.

However, platelet-rich plasma extracted from platelet-poor plasma (PPP) has a problem in that it has a low concentration of platelet. In addition, the prior art devices and methods for obtaining high-concentration plasma containing low-concentration platelet have a problem of low efficiency.

PRIOR ART DOCUMENT

Patent Documents

Patent Document 1: KR 10-2010-0116106
Patent Document 2: KR 10-2010-0041436

SUMMARY OF THE INVENTION

Accordingly, the present invention has been made in view of the problems occurring in the prior art, and it is an object of the present invention to provide a device and method of extracting high-concentration plasma from whole blood, in which high-concentration plasma, which contains a high concentration of platelet and contains or does not contain white blood cells, can be extracted from plasma using a simple filtration process by passing buffy coat-free or buffy coat-containing plasma, obtained by removing red blood cells from whole blood by centrifugation, through a membrane filter.

Another object of the present invention is to provide a device and method of extracting high-concentration plasma from whole blood, in which high-concentration plasma can be extracted by passing plasma, obtained by removing red blood cells from whole blood by primary centrifugation, through a membrane filter directly or after secondary centrifugation.

To achieve the above objects, in an embodiment, a device of extracting high-concentration plasma from whole blood comprises: a first syringe; a centrifugation tube that is connected to the first syringe in order to centrifuge whole blood received in the first syringe; a cap that is connected to the first syringe in order to re-centrifuge plasma collected in the first syringe by centrifugation of the whole blood; and a membrane filter comprising: a body that is cylindrical in shape and has a pair of spaced inlets to which the first syringe and a second syringe are to be respectively connected; a hollow membrane included in the body; and a first space formed between the body and the membrane and serving to collect components that passed through the membrane, wherein the device is configured such that the plasma resulting from the centrifugation or the re-centrifugation reciprocates one or more times through the first syringe and the second syringe while water or a water-containing component is removed from the plasma by the membrane, thereby extracting the high-concentration plasma.

Herein, the membrane filter may further comprise: plugs that configured to close both ends of the body while fixing the membrane by a fixing element protruding from one side thereof; and an outlet formed through the body so as to communicate the first space with the outside, and the membrane filter may be configured such that the plasma that flows to the first syringe and the second syringe through the inlets passes through the membrane via the plugs.

Further, the inner upper surface of the centrifugation tube may have a first curved portion so as to increase the volume of the tube space for receiving red blood cells and to discharge air from the tube space during centrifugation, and the portion of the centrifugation tube that is connected with the first outlet may have a first gap serving to prevent red blood cells received in the centrifugation tube from being agglomerated by surface tension and from flowing to the outside. In addition, the upper inner surface of the cap may have a second curved portion so as to increase the volume of the cap space for receiving red blood cells and to discharge air from the cap space during centrifugation, and the portion of the cap that is connected with the first outlet may have a second gap serving to prevent red blood cells received in the cap from being agglomerated by surface tension and from flowing to the outside.

Further, the membrane filter may preferably have a mesh size that is able to retain substances having a molecular weight of 40,000-60,000 Dalton, which is smaller than the molecular weight of albumin (66,000 Dalton), in order to remove water and an aqueous solution of uric acid and potassium from the plasma and to allow useful substances including albumin to remain in the plasma.

The whole blood may be received and centrifuged in the first syringe, a test tube, a test tube containing separation gel or a PRP kit.

In an embodiment of the present invention, a method of extracting high-concentration plasma from whole blood using the device according to the present invention comprises the steps of: (S10) collecting whole blood in a first syringe; (S11) connecting a centrifugation tube to the first syringe and centrifuging the whole blood collected in the first syringe; (S12) separating the centrifugation tube that has red blood cells received therein by the centrifugation; (S13) dropping buffy coat remaining in the first syringe to allow only plasma to remain in the first syringe; (S14) connecting the first syringe and a second syringe to a pair of inlets of a membrane filter, respectively; (S15) applying pressure to the first syringe to introduce the plasma from the first syringe into the membrane filter and allow the plasma to flow into the second syringe; (S16) introducing the plasma from the second syringe into the membrane filter and allowing the plasma to flow into the first syringe; (S17) repeating step (S15) and step (S16); and (S18) collecting high-concentration plasma containing components that are larger than a predetermined particle diameter and remain in the cavity of the membrane of the membrane filter without passing through the membrane.

In another embodiment, a method of extracting high-concentration plasma from whole blood using the device according to the present invention comprises the steps of: (S20) collecting whole blood in a first syringe; (S21) connecting a centrifugation tube to the first syringe and centrifuging the whole blood collected in the first syringe; (S22) separating the centrifugation tube that has red blood cells received therein by the centrifugation, so as to allow buffy coat-containing plasma to remain in the first syringe; (S23) connecting the first syringe and a second syringe to a pair of inlets of a membrane filter, respectively; (S24) applying pressure to the first syringe to introduce the buffy coat-containing plasma in the first syringe into the membrane filter and allow the plasma to flow into the second syringe; (S25) introducing the buffy coat-containing plasma from the second syringe into the membrane filter and allowing the plasma to flow into the first syringe; (S26) repeating step (S24) and step (S25); and (S27) collecting high-concentration plasma containing components that are larger than a predetermined particle diameter and remain in the cavity of the membrane of the membrane filter without passing through the membrane.

In still another embodiment, a method of extracting high-concentration plasma from whole blood using the device according to the present invention comprises the steps of: (S30) collecting whole blood in a first syringe; (S31) connecting a centrifugation tube to the first syringe and centrifuging the whole blood collected in the first syringe; (S32) separating the centrifugation tube that has red blood cells received therein by the centrifugation, so as to allow buffy coat-containing plasma to remain in the first syringe; (S33) connecting a cap to the first syringe and re-centrifuging the plasma received in the first syringe; (S34) separating the cap that has red blood cells received therein by the re-centrifugation; (S35) connecting the first syringe and a second syringe to a pair of inlets of a membrane filter, respectively; (S36) applying pressure to the first syringe to introduce concentrated plasma in the first syringe into the membrane filter and allow the plasma to flow into the second syringe; (S37) introducing the concentrated plasma from the second syringe into the membrane filter and allowing the plasma to flow into the first syringe; (S38) repeating step (S36) and step (S37); and (S39) collecting high-concentration plasma containing components that are larger than a predetermined particle diameter and remain in the cavity of the membrane of the membrane filter without passing through the membrane.

In still another embodiment, a device of extracting high-concentration plasma from whole blood using a device comprising a modified membrane filter according to the present invention comprises: a first syringe; a centrifugation tube that is connected to the first syringe in order to centrifuge whole blood received in the first syringe; and a membrane filter comprising: a body having an inlet to which the first syringe is to be connected; a membrane provided in a portion of the body; and a second space formed in the body, wherein the membrane filter is configured such that water or a water-containing component smaller than a predetermined particle diameter is removed from plasma, introduced in the second space, by the membrane, and high-concentration plasma containing components, which are larger than the predetermined particle diameter and do not pass through the membrane, remains in the second space.

Herein, the membrane filter may further comprise: an outlet formed at the bottom of the body so as to be opposite the inlet formed at the top of the body; a collection portion formed such that the second space communicates with the outside so that the components remaining in the second space formed in the inner upper portion of the body is collected in the outside; and an opening/closing element configured to open or close an outer end of the collection portion.

In yet another embodiment, a method of extracting high-concentration plasma from whole blood using a device comprising a modified membrane filter comprises the steps of: (S40) collecting whole blood in a first syringe; (S41) connecting a centrifugation tube to the first syringe and centrifuging the whole blood collected in the first syringe; (S42) separating the centrifugation tube that has red blood cells received therein by the centrifugation, so as to allow buffy coat-containing plasma to remain in the first syringe; (S43) connecting the first syringe to an inlet of a membrane filter; (S44) applying pressure to the first syringe to introduce the buffy coat-containing plasma from the first syringe into the membrane filter; and (S45) collecting high-concentration plasma containing components, which are larger than a predetermined particle diameter and remain in the second space without passing a membrane included in the membrane filter.

In addition, step (S45) may be performed by discharging and collecting the high-concentration plasma from the second space to the outside through either the inlet or a collection portion formed in the membrane filter so as to communicate the second space with the outside.

BRIEF DESCRIPTION OF THE DRAWINGS

The above and other objects, features and advantages of the present invention will be more clearly understood from the following detailed description taken in conjunction with the accompanying drawing, in which.

DETAILED DESCRIPTION OF THE INVENTION

Hereinafter, preferred embodiments of the present invention will be described in detail with reference to the accompanying drawings such that those skilled in the art can easily carry out the present invention. In the following description, a detailed description of known functions and configurations incorporated herein will be omitted when it may obscure the subject matter of the present invention.

A device of extracting high-concentration plasma from whole blood according to a preferred embodiment of the present invention will now be described with reference to the accompanying drawings.

Figure 2:
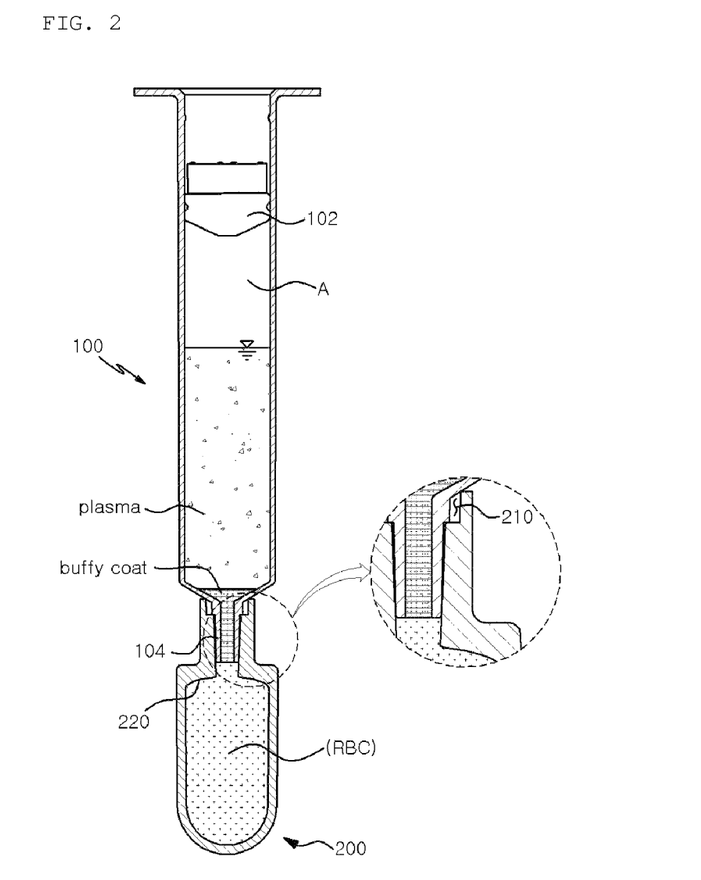
FIG. 2 is a side cross-sectional view schematically showing a syringe for centrifugation and a centrifugation tube in a device of extracting high-concentration plasma from whole blood according to a preferred embodiment of the present invention.
Figure 3:
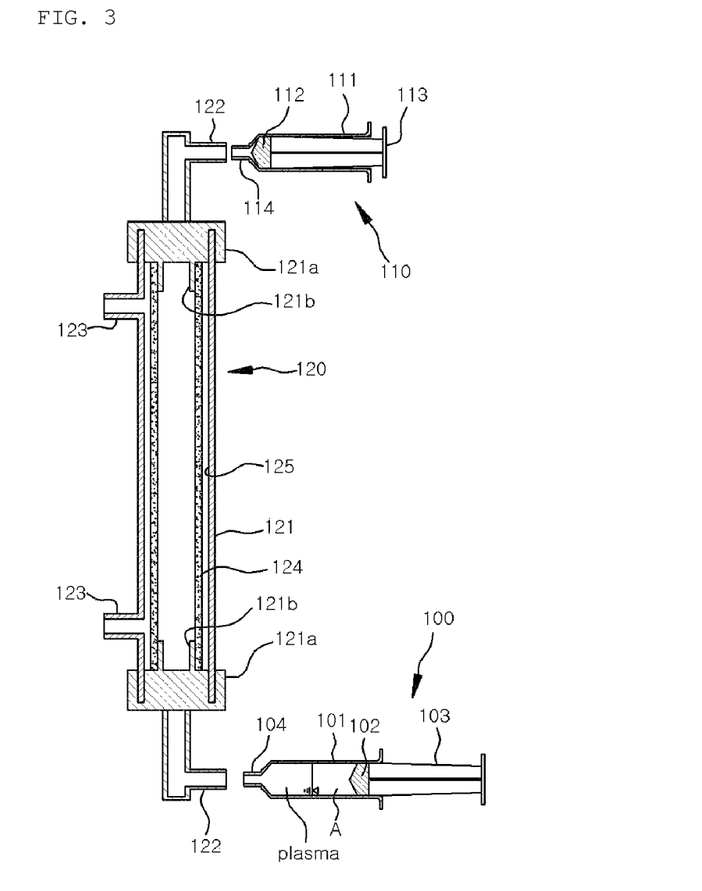
FIG. 3 is a side cross-sectional view schematically showing a syringe and a membrane filter in the device of FIG. 2.
Figure 4:
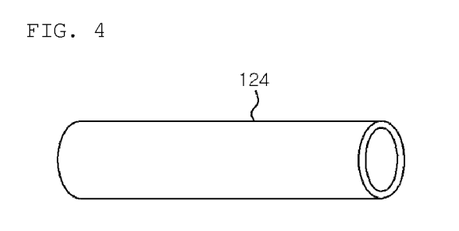
FIG. 4 is a side cross-sectional view schematically showing the membrane shown in FIG. 3.
Figure 5:
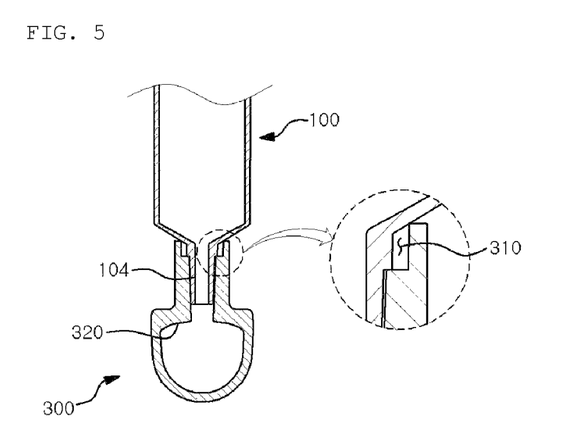
FIG. 5 is a side cross-sectional view schematically showing a syringe and a cap in the device of FIG. 2.

FIG. 2 is a side cross-sectional view schematically showing a syringe for centrifugation and a centrifugation tube in a device of extracting high-concentration plasma from whole blood according to a preferred embodiment of the present invention; FIG. 3 is a side cross-sectional view schematically showing a syringe and a membrane filter in the device of FIG. 2; FIG. 4 is a side cross-sectional view schematically showing the membrane shown in FIG. 3; and FIG. 5 is a side cross-sectional view schematically showing a syringe and a cap in the device of FIG. 2.

As shown in FIGS. 2 to 5, the extraction device according to the present invention comprises a first syringe 100, a second syringe 110, a membrane filter 120, a centrifugation filter 200 and a cap 300.

As shown in FIGS. 2 and 3, the first and second syringes 100 and 110 comprise first and second cylinders 101 and 111, first and second rubber packings 102 and 112, first and second plungers 103 and 113 and a needle (not shown). For convenience of explanation, the syringe from which the needle was removed is shown in the drawings and will now be described.

The first syringe 100 is an element serving to collect and receive whole blood (Wb). A centrifugation tube 200 is connected to a first outlet 104 of the first syringe 100 in order to perform primary centrifugation. In addition, a cap 300 is connected to the first outlet 104 in order to perform secondary centrifugation for removing a trace amount of red blood cells after primary centrifugation. Particularly, the cap 300 is connected to one inlet of a pair of inlets 122 of a membrane filter 120 for filtering plasma.

In the first syringe 100 having whole blood (Wb) received therein, the first rubber packing 102 and the first plunger 103 are pushed backward from the first outlet 104 as shown in FIG. 2. In order to centrifuge the content of the first syringe 100, the centrifugation tube 200 is connected to the first outlet 104.

After primary centrifugation, the centrifugation tube 200 having red blood cells received therein is separated, and when buffy coat is to be discharged from the first syringe 100 containing collected plasma and buffy coat, the buffy coat is dropped using the first plunger 103 of the first syringe 100.

In addition, the first outlet 104 is connected to one inlet of a pair of inlets 122 of the membrane filter 120 such that the plasma (or plasma and buffy coat) received in the first syringe 100 can pass through the membrane filter 120.

In addition, a predetermined amount of air A is received in the first syringe 100 having plasma (or plasma and buffy coat) received therein. Air A serves to facilitate the introduction of plasma, which passed through the membrane filter 120, into the second syringe 110. For example, the ratio between plasma and air A, which are received in the first syringe 100, is preferably about 1:1, and in addition, the amount of air in the first syringe 100 can be adjusted such that plasma can completely flow from the first syringe 100 into the second syringe 110.

The first syringe 100 serves to receive and centrifuge whole blood. In place of the first syringe 100, a conventional test tube, a test tube containing separation gel, or a PRP kit may be used. In other words, centrifugation of whole blood may be performed using various tools and methods.

The second syringe 110 serves to receive plasma that passed through the membrane filter 120 from the first syringe 100. The second outlet 114 of the second syringe 120 is connected to the other inlet 122 of a pair of inlets 122 of the membrane filter 120. As shown in FIG. 3, the second rubber packing 112 and second plunger 113 of the second plunger 120 are located at the side of the second outlet 114 in order to receive platelet-poor plasma (PPP).

Thus, when the first plunger 103 of the first syringe 100 is pressed downward, plasma is introduced into the second syringe 110 through the membrane filter 110 while the second plunger 113 of the second syringe 110 is pushed backward. Then, when the second plunger 113 is pressed, plasma received in the second syringe 110 flows into the first syringe 100. Thus, when the first plunger 103 and the second plunger 113 are alternately pressed, plasma passes through the membrane filter 120 while it reciprocates, and through this process, components smaller than a predetermined particle diameter, including water, uric acid, potassium and phosphate, are separated from the plasma. Then, the remaining plasma containing components larger than the predetermined particle diameter, including protein and albumin, is collected in the first syringe 100 or the second syringe 110.

The membrane filter 120 comprises a body 121, two inlets 122, outlets 123, a membrane 124 and a first space 125. The membrane filter 120 may have an adjusted mesh size and serves to separate components smaller than a predetermined particle diameter, including water, uric acid, potassium and phosphate, from plasma while leaving useful components larger than the predetermined particle diameter, including protein and albumin. The membrane filter 120 that is used in the present invention may be a membrane filter for blood dialysis or a modification thereof.

The body 121 is approximately cylindrical in shape, includes the membrane 124 and has plugs 121a so as to communicate the body with the inlets 122. In other words, the body 121 is configured such that the plasma introduced through the inlets 122 passes through the membrane 124 via the plugs 121a. As shown in FIG. 3, a fixing member 121b protruding from one side of the plug 121a is inserted into the cavity of the membrane 124 to fix the membrane 124.

Moreover, a pair of the inlets 122 are provided at the side of the body 121 such that the first syringe 100 and the second syringe are arranged in the same direction. The inlets 122 are preferably formed upward from the body 121.

In addition, the outlets 123 are formed downward from the body 121 such that components, separated from plasma by the membrane 124 and smaller than a predetermined particle diameter, including water, uric acid, potassium and phosphate, can be discharged to the outside. One or a plurality of outlets 123 may be formed, and the outlets 123 are preferably formed at both sides of the body 121, respectively.

The membrane 124 is a membrane serving to extract high-concentration plasma containing protein and albumin from plasma. As shown in FIG. 4, the membrane 124 has a hollow cylindrical shape and is included in the body 121 such that plasma can flow along the cavity of the membrane. Preferably, the membrane 124 is a circular shape having an inner diameter of 200-300 µm and a thickness of 40-50 µm, comprises about 50-1000 membrane fibers included in the filter body and has an effective cross-sectional area of about 0.01-0.014 m$^2$. More preferably, the membrane 124 has a mesh size that retain substances having a molecular weight of 40,000-60,000 Dalton, which is smaller than the molecular weight of albumin (66,000 Dalton). The membrane 124 is preferably a membrane for blood dialysis.

Meanwhile, the first space 125 is provided between the inner surface of the body 121 and the outer surface of the membrane 124. The first space 125 is configured such that components, discharged from the membrane 124 and smaller than a predetermined particle diameter, can be collected and can easily flow to the outlet 123.

The centrifugation tube 200 is a member that is connected to the first outlet 104 of the first syringe 100 and serves red blood cells (RBCs) collected from whole blood by primary centrifugation. It is separated from the first outlet 104 after primary centrifugation. In other words, the centrifugation tube 200 is connected to the first syringe 100 in order to perform primary centrifugation and is separated from the first syringe 100 before the first syringe 100 is connected to the membrane filter 120. The upper inner surface of the centrifugation tube 200 has a first curved portion 220 in order to increase the volume of the space for receiving red blood cells (RBCs) and to allow air in the space to be completely discharged to the outside during primary centrifugation. In addition, the portion of the centrifugation tube 200 that is connected to the first outlet 104 has a first gap 210 that serves to prevent the red blood cells (RBCs) received in the centrifugation tube 200 from being agglomerated by surface tension and from flowing to the outside.

The cap 300 is connected to the first outlet 104 of the first syringe 100 when secondary centrifugation following primary centrifugation is to be performed. It serves to receive red blood cells (RBCs) collected by secondary centrifugation. In addition, the cap 300 is connected to the first outlet 104 in order to remove a trace amount of red blood cells from plasma after primary centrifugation. When buffy coat is dropped, the cap 300 may not be used. In addition, the upper inner surface of the cap 300 has a second curved portion 320 in order to increase the volume of the space for receiving red blood cells (RBCs) and to allow air in the space to be completely discharged to the outside during primary centrifugation. Additionally, the portion of the cap 300 that is connected to the first outlet 104 has a second gap 310 that serves to prevent the red blood cells (RBCs) received in the cap 300 from being agglomerated by surface tension and from flowing to the outside.

Method 1

The inventive method of extracting high-concentration plasma by separating buffy coat and red blood cells from whole blood by primary centrifugation and passing the plasma collected in the first syringe through the membrane filter will now be described in detail with reference to the accompanying drawings.

Figure 6:
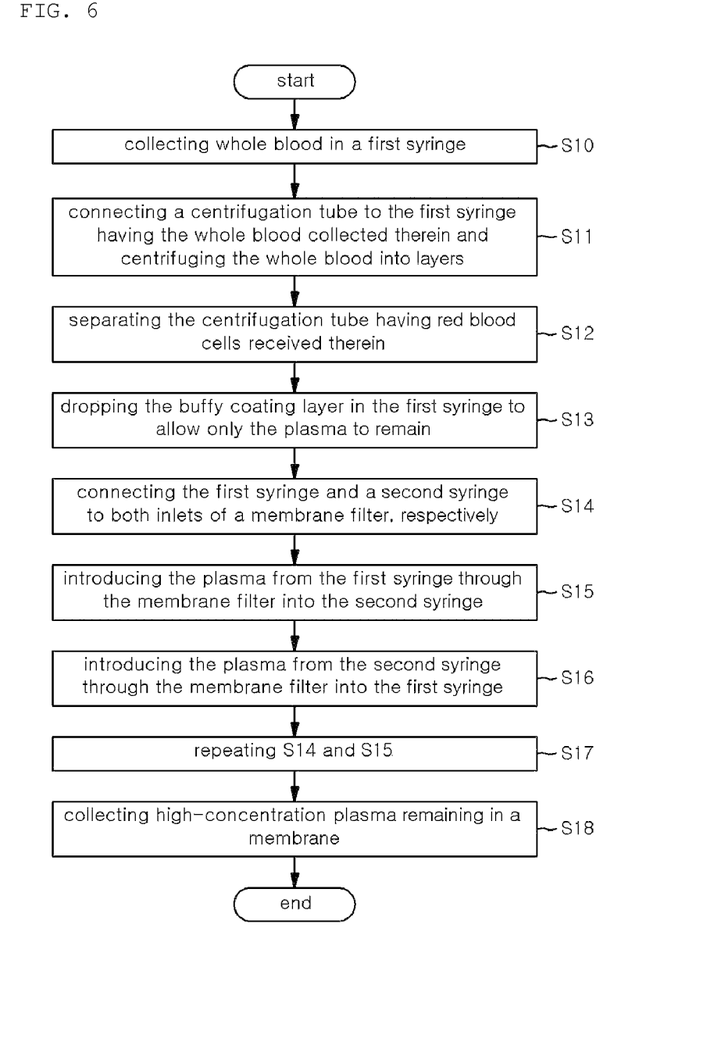
FIG. 6 is a flowchart schematically showing a method of extracting high-concentration plasma using the device of FIG. 2.

FIG. 6 is a flowchart schematically showing a method of extracting high-concentration plasma using the device of FIG. 2.

First, whole blood is collected in the first syringe 100 (S10).

Then, the centrifugation tube 200 is connected to the first syringe 100, and centrifugation of the whole blood is performed (S11). Specifically, the centrifugation tube 200 is connected to the first outlet 104 of the first syringe 100, and the whole blood in the first syringe 100 connected to the centrifugation tube 200 is centrifuged. This centrifugation separates the whole blood into a red blood cell (RBC) layer, a platelet-rich plasma layer containing buffy coat and a platelet-poor plasma (PRP) layer. Herein, the red blood cells are received in the centrifugation tube 200. The internal space of the centrifugation tube 200 is formed in consideration of the amount of red blood cells that are separated from whole blood. In other words, red blood cells are received in the centrifugation tube 200, and buffy coat is located in the first outlet 104 of the first syringe 100.

Next, the centrifugation tube 200 containing red blood cells received therein is separated (S12). After completion of the centrifugation, the centrifugation tube 200 having red blood cells received therein is separated from the first syringe 100. Thus, the first syringe 100 has buffy coat-containing plasma collected therein.

Then, the buffy coat is dropped so that only the plasma is allowed to remain in the first syringe 100 (S13). When the centrifugation tube 200 is separated, the buffy coat is then located in the lowest portion corresponding to the first outlet 104 of the first syringe 100. The buffy coat in the first outlet 104 is dropped using the first plunger 103 so that only the plasma is allowed to remain in the first syringe 100.

Next, the first syringe 100 and the second syringe 110 are connected to a pair of the inlets 122 of the membrane filter 120, respectively (S14). Herein, the first outlet 104 of the first syringe 100 is connected to one inlet 122 of the membrane filter 120, and the second outlet 114 of the second syringe 110 is connected to the other inlet 122 of the membrane filter 120.

Then, pressure is applied so that the plasma in the first syringe 100 is injected into the membrane filter 120 and allowed to flow into the second syringe 110 (S15). Herein, the plasma introduced into the membrane filter 120 flows through the cavity portion of the membrane 124. At this time, the plasma is separated into components smaller than a predetermined particle diameter, including water, uric acid, potassium and phosphate, and components larger than the predetermined particle diameter, including protein and albumin. In other words, the components smaller than the predetermined particle diameter are collected in the first space 125, and then discharged to the outside through the outlet 123, and the components larger than the predetermined particle diameter remain in the plasma and flow into the second syringe 110.

Then, the plasma received in the second syringe 110 is introduced into the membrane filter 120 and allowed to flow into the first syringe 100 (S16). It is to be understood that this process is performed in the same manner as the previous step (S15). The membrane 124 has a mesh size of 40,000-60,000 Dalton so that albumin having a molecular weight of 66,000 Dalton remains in the plasma. Preferably, the membrane 124 is a circular shape having an inner diameter of 200-300 µm and a thickness of 40-50 µm, comprises about 50-1000 membrane fibers included in the filter body and has an effective cross-sectional area of about 0.01-0.014 m². More preferably, the membrane 124 has a mesh size that can retain substances having a molecular weight of 40,000-60,000 Dalton, which is smaller than the molecular weight of albumin (66,000 Dalton). The membrane 124 is preferably a membrane for blood dialysis.

Next, step (S15) and step (S16) are repeated (S17). Step (S17) is repeated until the components, collected in the first space 125 and smaller than the predetermined particle diameter, are completely discharged to the outside through the outlet 123. Thus, the plasma that flows so as to be received alternately in the first syringe 100 and the second syringe 110 changes to high-concentration plasma because water or water-containing components smaller than a predetermined particle diameter are separated therefrom.

Finally, high-concentration plasma is collected, which is larger than the predetermined particle diameter and remains in the cavity of the membrane 124 without passing through the membrane 124 (S18). In this step, the first syringe 100 is sufficiently pressurized so that components larger than the predetermined particle diameter are completely received in the second syringe 110. It is to be understood that the second syringe 110 may also be pressurized so that components larger than the predetermined particle diameter are received in the first syringe 100.

The above-described method 1 is a process for obtaining high-concentration plasma from plasma obtained by separating red blood cells from whole blood, unlike a conventional method of obtaining platelet-rich plasma from platelet-poor plasma. This process is simpler than a conventional centrifugation or filtration process for collecting platelet rich plasma (PRP) and concentrated plasma and can collect a larger amount of high-concentration plasma with a higher purity compared to that obtainable by a conventional method.

Method 2

The inventive method of extracting high-concentration plasma by separating red blood cells from whole blood by primary centrifugation and passing the buffy coat and plasma collected in the first syringe through the membrane filter will now be described in detail with reference to the accompanying drawings.

Figure 7:
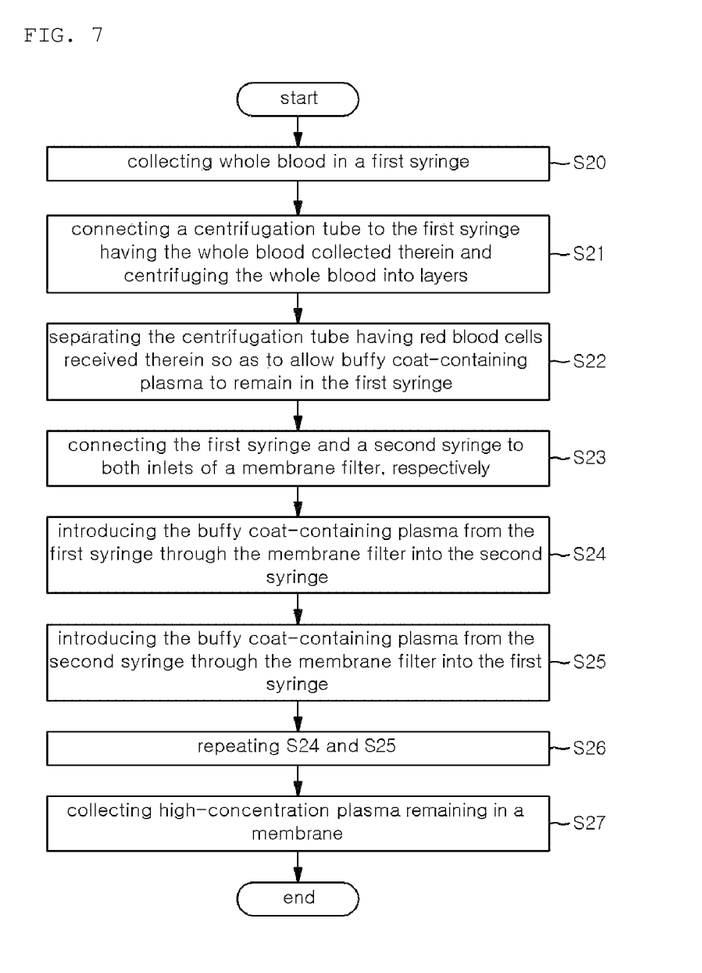
FIG. 7 is a flowchart schematically showing another method of extracting high-concentration plasma using the device of FIG. 2.

FIG. 7 is a flowchart schematically showing another method of extracting high-concentration plasma using the device of FIG. 2.

First, whole blood is collected in the first syringe 100 (S20).

Then, the centrifugation tube 200 is connected to the first syringe 100, and centrifugation of the whole blood is performed (S21). Specifically, the centrifugation tube 200 is connected to the first outlet 104 of the first syringe 100, and the whole blood in the first syringe 100 connected to the centrifugation tube 200 is centrifuged. This centrifugation separates the whole blood into a red blood cell (RBC) layer, a platelet-rich plasma layer containing buffy coat and a platelet-poor plasma (PRP) layer. Herein, the red blood cells are received in the centrifugation tube 200. The internal space of the centrifugation tube 200 is formed in consideration of the amount of red blood cells that are separated from whole blood. In other words, red blood cells are received in the centrifugation tube 200, and buffy coat is located in the first outlet 104 of the first syringe 100.

Next, the centrifugation tube 200 containing red blood cells received therein is separated, and the plasma containing buffy coat is allowed to remain in the first syringe 100 (S22). After completion of the centrifugation, the centrifugation tube 200 having red blood cells received therein is separated from the first syringe 100. Thus, the first syringe 100 has buffy coat-containing plasma collected therein.

Next, the first syringe 100 and the second syringe 110 are connected to a pair of the inlets 122 of the membrane filter 120, respectively (S23). Herein, the first outlet 104 of the first syringe 100 is connected to one inlet 122 of the membrane filter 120, and the second outlet 114 of the second syringe 110 is connected to the other inlet 122 of the membrane filter 120.

Then, pressure is applied so that the buffy coat-containing plasma in the first syringe 100 is introduced into the membrane filter 120 and allowed to flow into the second syringe 110 (S24). Herein, the plasma introduced into the membrane filter 120 flows through the cavity portion of the membrane 124. At this time, the plasma is separated into components smaller than a predetermined particle diameter, including water, uric acid, potassium and phosphate, and components larger than the predetermined particle diameter, including protein and albumin. In other words, the components smaller than the predetermined particle diameter are collected in the first space 125, and then discharged to the outside through the outlet 123, and the components larger than the predetermined particle diameter remain in the plasma and flow into the second syringe 110.

Then, the plasma received in the second syringe 110 is introduced into the membrane filter 120 and allowed to flow into the first syringe 100 (S25). It is to be understood that this process is performed in the same manner as the previous step (S24). Preferably, the membrane 124 has a mesh size that can retain substances having a molecular weight of 40,000-60,000 Dalton, which is smaller than the molecular weight of albumin (66,000 Dalton).

Next, step (S24) and step (S25) are repeated (S26). Step (S26) is repeated until the components, collected in the first space 125 and smaller than the predetermined particle diameter, are completely discharged to the outside through the outlet 123. Thus, the plasma that flows so as to be received alternately in the first syringe 100 and the second syringe 110 changes to high-concentration plasma, because water or water-containing components smaller than a predetermined particle diameter are separated therefrom.

Finally, high-concentration plasma is collected, which is larger than the predetermined particle diameter and remains in the cavity of the membrane 124 without passing through the membrane 124 (S27). In this step, the first syringe 100 is sufficiently pressurized so that components larger than the predetermined particle diameter are completely received in the second syringe 110. It is to be understood that the second syringe 110 may also be pressurized so that components larger than the predetermined particle diameter are received in the first syringe 100.

The above-described method 2 can collect a larger amount of high-concentration plasma with a higher purity compared to that obtainable by a conventional method.

Method 3

The inventive method of extracting high-concentration plasma by separating red blood cells from whole blood by primary centrifugation, separating red blood cells from the buffy coat and plasma collected in the first syringe by secondary centrifugation and then passing the resulting plasma through the membrane filter will now be described in detail.

Figure 8:
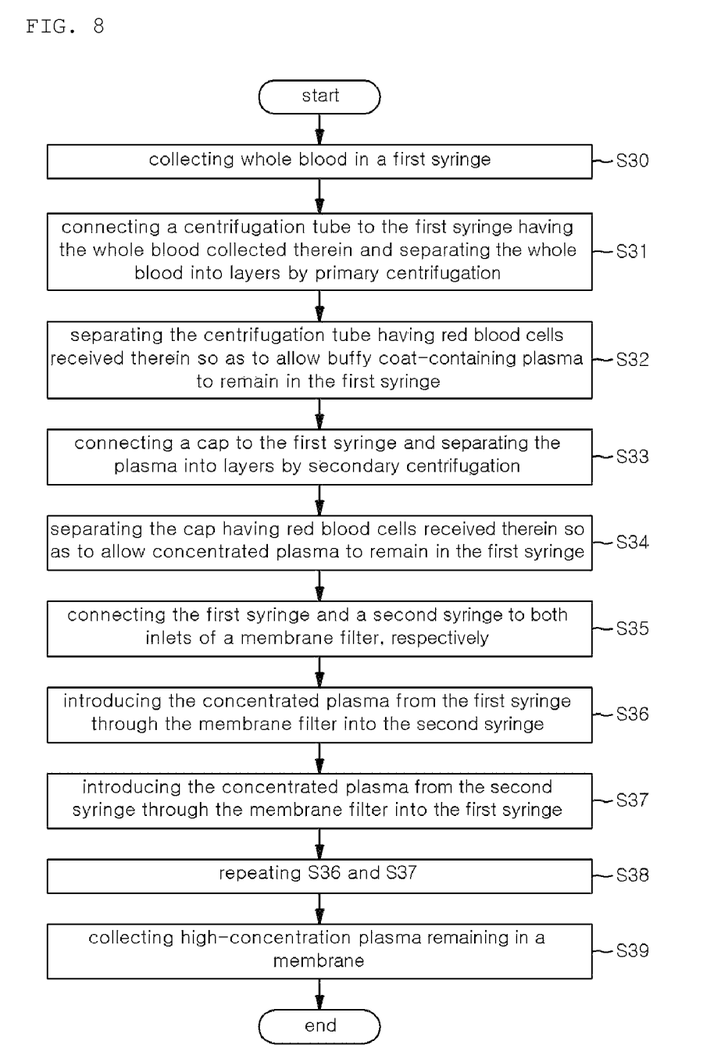
FIG. 8 is a flowchart schematically showing a method of extracting high-concentration plasma using the devices of FIGS. 2 and 5.

FIG. 8 is a flowchart schematically showing a method of extracting high-concentration plasma using the devices of FIGS. 2 and 5.

First, whole blood is collected in the first syringe 100 (S30).

Then, the centrifugation tube 200 is connected to the first syringe 100, and centrifugation of the whole blood is performed (S31). Specifically, the centrifugation tube 200 is connected to the first outlet 104 of the first syringe 100, and the whole blood in the first syringe 100 connected to the centrifugation tube 200 is centrifuged. This centrifugation separates the whole blood into a red blood cell (RBC) layer, a platelet-rich plasma layer containing buffy coat and a platelet-poor plasma (PRP) layer. Herein, the red blood cells are received in the centrifugation tube 200. The internal space of the centrifugation tube 200 is formed in consideration of the amount of red blood cells that are separated from whole blood. In other words, red blood cells are received in the centrifugation tube 200, and buffy coat is located in the first inlet 104 of the first syringe 100.

Next, the centrifugation tube 200 containing red blood cells received therein is separated (S32), and the buffy coat-containing plasma is allowed to remain in the first syringe 100. After completion of the primary centrifugation, the centrifugation tube 200 having red blood cells received therein is separated from the first syringe 100. Thus, the first syringe 100 has buffy coat-containing plasma collected therein.

Next, the cap 300 is connected to the first syringe 100, and the content of the first syringe 100 is subjected to secondary centrifugation (S33). Specifically, after completion of the primary centrifugation, the cap 300 is connected to the first outlet of the first syringe 100, and the content of the first syringe 100 connected to the cap 300 is centrifuged. As a result, a trace amount of red blood cells are separated from the buffy coat-containing plasma received in the first syringe 100. After the secondary concentration, a small amount of red blood cells are received in the cap 300, and the cap 300 is separated from the first syringe 100.

Then, the cap 300 having red blood cells received therein is separated (S34). After the secondary centrifugation, the cap 300 having red blood cells received therein is separated from the first syringe 100. As a result, the first syringe 100 has received therein dark yellow concentrated plasma from which red blood cells were completely removed.

Next, the first syringe 100 and the second syringe 110 are connected to a pair of the inlets 122 of the membrane filter 120, respectively (S35). Herein, the first outlet 104 of the first syringe 100 is connected to one inlet of the membrane filter 120, and the second outlet 114 of the second syringe 110 is connected to the other inlet 122 of the membrane filter 120.

Then, pressure is applied so that the concentrated plasma in the first syringe 100 is introduced into the membrane filter 120 and allowed to flow into the second syringe 110 (S35). Herein, the concentrated plasma introduced into the membrane filter 120 flows through the cavity portion of the membrane 124. At this time, the concentrated plasma is separated into components smaller than a predetermined particle diameter, including water, uric acid, potassium and phosphate, and components larger than the predetermined particle diameter, including protein and albumin. In other words, the components smaller than the predetermined particle diameter are collected in the first space 125, and then discharged to the outside through the outlet 123, and the components larger than the predetermined particle diameter remain in the concentrated plasma and flow into the second syringe 110.

Then, the concentrated plasma received in the second syringe 110 is introduced again into the membrane filter 120 and allowed to flow into the first syringe 100 (S37). It is to be understood that this process is performed in the same manner as the previous step (S36). The membrane 124 has a mesh size that can retain substances having a molecular weight of 40,000-60,000 Dalton, so that albumin having a molecular weight of 6,000 Dalton remains in the plasma.

Next, step (S36) and step (37) are repeated (S38). Step (S38) is repeated until the components, collected in the first space 125 and smaller than the predetermined particle diameter, are completely discharged to the outside through the outlet 123. Thus, the plasma that flows so as to be received alternately in the first syringe 100 and the second syringe 110 changes to high-concentration plasma, because water or water-containing components smaller than a predetermined particle diameter are separated therefrom.

Finally, high-concentration plasma is collected, which is larger than the predetermined particle diameter and remains in the cavity of the membrane 124 without passing through the membrane 124 (S39). In this step, the first syringe 100 is sufficiently pressurized so that components larger than the predetermined particle diameter are completely received in the second syringe 110. It is to be understood that the second syringe 110 may also be pressurized so that components larger than the predetermined particle diameter are received in the first syringe 100.

The above-described method 3 can collect a larger amount of high-concentration plasma with a higher purity compared to that obtainable by a conventional method. In method 1 and method 2, centrifugation is performed once, and thus a small amount of red blood cells remain in the obtained plasma, but in method 3, centrifugation is performed twice, and thus the obtained plasma is completely free of red blood cells and is deep yellow concentrated plasma.

Modified Embodiment of Membrane Filter

A modified embodiment of the present invention will be described in detail with reference to the accompanying drawings.

Figure 9:
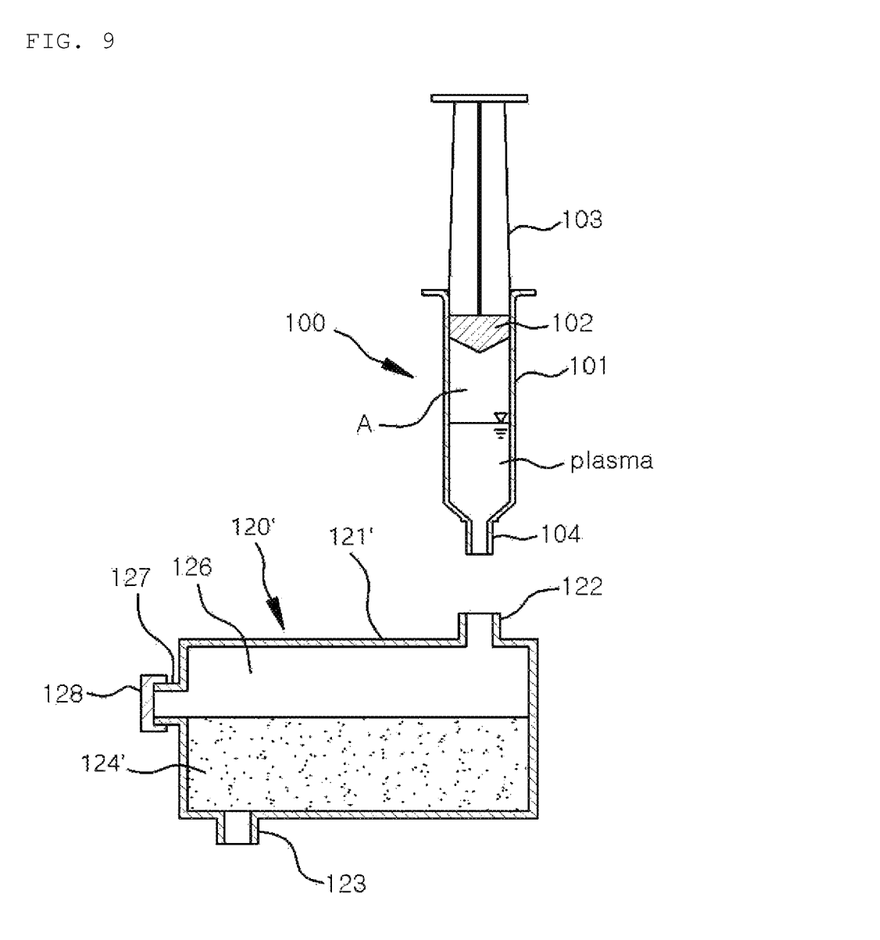
FIG. 9 is a side cross-sectional view schematically showing an example of the membrane filter shown in FIG. 3.

FIG. 9 is a side cross-sectional view schematically showing a modified embodiment of the membrane filter shown in FIG. 3. In the following description, like elements in the membrane filter shown in FIG. 3 will be indicated by like reference numerals. In the following description of the modified embodiment, the same elements as those of the membrane filter in FIG. 3 will be briefly described, if necessary, and the description will be concentrated on a structure different from that of the membrane filter.

As shown in FIG. 9, a membrane filter 120' comprises a body 121', an inlet 122, an outlet 123, a second space 126, a membrane 124' and a collection portion 127. The membrane filter 120' functions in the same manner as that of FIG. 3 and has a modified structure.

The body 121' is approximately rectangular in shape, has an inlet 122 formed at the top and an outlet 123 formed at the bottom, and includes a membrane 124' provided in the inner lower portion and a second space 126 formed in the inner upper portion. In addition, the body 121' includes a collection portion 127 through which the second space 126 communicates with the outside.

Further, one or a plurality of inlets 122 is formed at the top of the body 121'. Preferably, one inlet is formed at the top so as to extend upward from the body 121'. To the inlet 122, the first outlet 104 of the first syringe 100 is connected.

In addition, one or a plurality of outlets 123 is formed at the bottom of the body 121'. Preferably, one outlet 123 is formed at the bottom of the body 121' so as to extend downward from the bottom. The position of the outlet 123 is preferably symmetric to the position of the inlet 122. Through the outlet 123, components, passed through the membrane 124' and smaller than a predetermined particle diameter, are discharged to the outside. In addition, the lower inner surface of the membrane filter 120 may also be formed to slope toward the outlet 123 so that the components that passed through the membrane 124' easily flow to the outlet 123. To the outlet 123, a separate syringe for receiving components smaller than a predetermined particle diameter may also be connected.

The second space 126 serves to temporarily store the plasma introduced through the inlet 122 and is formed so as to ensure the maximum contact area between the plasma and the membrane 124' so that the plasma temporarily stored in the second space 126 is passed through the membrane 124' by gravity and the pressure applied to the first syringe 100.

The second space 126 is provided in order to allow plasma components smaller than a predetermined particle diameter, including water, uric acid, potassium and phosphate, to pass through the membrane 124' while allowing concentrated plasma, larger than the predetermined particle diameter and including protein and albumin, to remain in the second space 126.

The membrane 124' is provided in the inner lower portion of the membrane filter 120. The membrane 124' functions in the same manner as the membrane 124 shown in FIG. 3 and has a shape different from that of FIG. 3. In other words, the membrane 124' functions to separate the plasma into components smaller than a predetermined particle diameter and components larger than the predetermined particle diameter so as to filter concentrated plasma from the plasma.

The collection portion 127 is configured to communicate with the second space 126, and the outer end thereof is selectively opened or closed by an opening/closing element 128. The collection portion 127 is provided in order to discharge concentrated plasma containing protein and albumin, which remains in the second space 126 without passing through the membrane 124', from the second space 126 to the outside. It is to be understood that the collection portion 127 is closed by the opening/closing element 128 in a state in which the second space 126 has the plasma received therein, and the collection portion 127 is opened by the opening/closing element 128 in a state in which only concentrated plasma remains in the second space 126, so that the concentrated plasma is discharged to the outside.

Method 4

The inventive method of extracting high-concentration plasma from whole blood using the modified membrane filter will now be described in detail with reference to the accompanying drawings.

Figure 10:
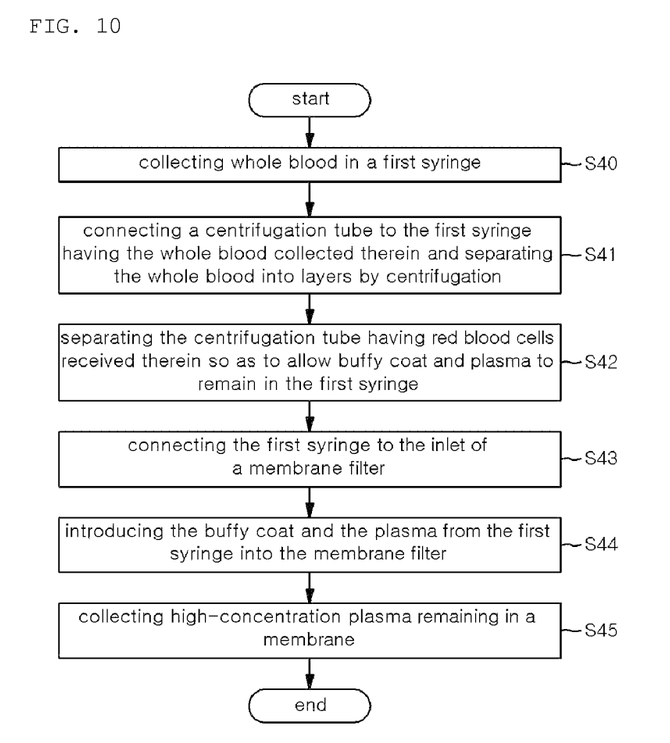
FIG. 10 is a flowchart schematically showing another method of extracting high-concentration plasma using the device of FIG. 9.

FIG. 10 is a flowchart schematically showing a method of extracting high-concentration plasma using the device of FIG. 9.

First, whole blood (Wb) is collected in the first syringe 100 (S40).

Then, the centrifugation tube 200 is connected to the first syringe 100, and centrifugation of the whole blood is performed (S41). Specifically, the centrifugation tube 200 is connected to the first outlet 104 of the first syringe 100, and the whole blood in the first syringe 100 connected to the centrifugation tube 200 is centrifuged. This centrifugation separates the whole blood into a red blood cell (RBC) layer, a platelet-rich plasma layer containing buffy coat and a platelet-poor plasma (PRP) layer. Herein, the red blood cells are received in the centrifugation tube 200. The internal space of the centrifugation tube 200 is formed in consideration of the amount of red blood cells that are separated from whole blood. In other words, red blood cells are received in the centrifugation tube 200, and buffy coat is located in the first outlet 104 of the first syringe 100.

Next, the centrifugation tube 200 containing red blood cells received therein is separated, and buffy coat-containing plasma is allowed to remain in the first syringe 100 (S42). After completion of the centrifugation, the centrifugation tube 200 having red blood cells received therein is separated from the first syringe 100. Thus, the first syringe 100 has buffy coat-containing plasma collected therein.

Then, the first syringe 100 is connected to the inlet 122 of the membrane filter 120' (S43). Specifically, the first inlet 104 of the first syringe 100 is connected to the inlet 122 of the membrane filter 120'.

Then, pressure is applied so that the buffy coat-containing plasma in the first syringe 100 is introduced into the membrane filter 120' (S44). After the plasma is introduced into the membrane filter 120', components smaller than a predetermined particle diameter, including water, uric acid, potassium and phosphate, pass through the membrane 124', and components larger than the predetermined particle diameter, including protein and albumin, remain in the second space 126. Herein, the membrane 124 has a mesh size that can retain substances having a molecular weight of 40,000-60,000 Dalton, which is smaller than the molecular weight of albumin 66,000 (Dalton).

Finally, high-concentration plasma is collected, which is larger than the predetermined particle diameter and remains in the membrane 124' without passing through the membrane 124' (S45). To collect the high-concentration plasma from the second space 126, the first syringe 100 is separated from the membrane filter 120', after which the membrane filter 120' is inclined in one direction, and the high-concentration plasma is collected in a separate element through the inlet 122 or the collection portion 127. The separate element for collecting the high-concentration plasma may be the first syringe 100 or a separate syringe.

The above-described method 4 can collect a larger amount of high-concentration plasma with a higher purity compared to that obtainable by a conventional method.

As described above, according to the present invention, high-concentration plasma including plasma, concentrated platelet, protein and fibrin can be extracted by a simple process within a short time by either centrifuging whole blood received in a PRP kit, a test tube or a test tube containing separation gel to collect PRP or PPP or passing plasma, obtained by removing red blood cells from whole blood, through the membrane filter.

Furthermore, high-concentration plasma, which contains useful components, including albumin and globulin, and has a plasma concentration at least four times higher than that of platelet-poor plasma, can be obtained by separating water, uric acid and the like from plasma, collected from whole blood, using the membrane filter.

Moreover, high-concentration plasma with or without white blood cells can be obtained by passing buffy coat-free plasma or buffy coat-containing plasma, obtained by centrifuging whole blood, through the membrane filter.

In addition, high-concentration plasma having a deep yellow color can be obtained by centrifuging buffy coat-containing plasma, remaining after centrifugation of whole blood, to remove a trace amount of red blood cells therefrom, and then passing the resulting plasma through the membrane filter.

Additionally, because high-concentration plasma can be collected even by a simple filtration process alone, various kinds of concentrated plasma can be obtained. Further, the process of the method of the present invention is simpler than a conventional process for collecting platelet-rich plasma (PRP) and concentrated plasma and is highly efficient in terms of time and quality.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A kit for extracting high-concentration plasma from whole blood, the kit comprising:
   a first syringe including a first outlet;
   a centrifugation tube configured for direct connection to the first outlet of the first syringe in order to centrifuge whole blood received in the first syringe,
   wherein an inner upper surface of the centrifugation tube has a first curved portion configured to increase a volume of the centrifugation tube for receiving red blood cells and to discharge air from the centrifugation tube during a primary centrifugation, and a portion of the centrifugation tube configured for direction connection to the first outlet of the first syringe, and
   wherein the portion of the centrifugation tube has a first gap serving to prevent red blood cells received in the centrifugation tube from being agglomerated by surface tension and from flowing to outside the centrifugation tube;
   a cap configured for direct connection to the first outlet of the first syringe and configured to re-centrifuge plasma,
   wherein the cap is smaller than the centrifugation tube in length,
   wherein an inner upper surface of the cap has a second curved portion configured to increase a volume of the cap for receiving red blood cells and to discharge air from the cap during a secondary centrifugation, and a portion of the cap configured for direction connection to the first outlet of the first syringe, and
   wherein the portion of the cap has a second gap serving to prevent red blood cells received in the cap from being agglomerated by surface tension and from flowing to outside the cap; and
   a membrane filter comprising:
     a cylindrical body including: a first inlet configured to receive the first syringe, a second inlet configured to receive a second syringe, and an outlet;
     a hollow cylindrical membrane located within the cylindrical body and substantially coaxial with the cylindrical body, wherein the hollow cylindrical membrane defines an internal cavity configured to pass plasma in a primarily axial direction from the first inlet to the second inlet, and configured to pass plasma in an opposite primarily axial direction from the second inlet to the first inlet; and
     a first space formed between the cylindrical body and the hollow cylindrical membrane, wherein the first space is configured to receive water and small components from the internal cavity that are filtered in a substantially radial direction through the hollow cylindrical membrane, thereby increasing a concentration of large components inside the internal cavity each time that plasma is passed from the first inlet to the second inlet or from the second inlet to the first inlet.

2. The kit of claim 1, wherein the membrane filter further comprises:
   a first plug configured to hold a first end of the hollow cylindrical membrane internally and coaxially with a first end of the cylindrical body, and configured to provide unfiltered fluid communication between the first inlet and the internal cavity; and
   a second plug configured to hold a second end of the hollow cylindrical membrane internally and coaxially with a second end of the cylindrical body, and configured to provide unfiltered fluid communication between the second inlet and the internal cavity, and
   wherein the first and second plugs are configured to prevent unfiltered fluid communication between the internal cavity and the first space.

3. The kit of claim 1, wherein the membrane filter has a mesh size that is able to retain substances having a molecular weight of 40,000-60,000 Dalton, which is smaller than the molecular weight of albumin (66,000 Dalton), in order to allow substances including albumin to remain in the plasma.

4. The kit of claim 1, further comprising a separation gel.

5. A kit for extracting high-concentration plasma from whole blood, the kit comprising:
   a first syringe;
   a centrifugation tube configured for direct connection to the first syringe and configured to centrifuge whole blood received in the first syringe; and
   a membrane filter comprising:
     a body having an inlet located at a top of the body and configured to receive the first syringe;
     a membrane located within the body and separating an internal region of the body into an upper portion and a lower portion, wherein the upper portion is an unfiltered space and the lower portion is a filtered space, and the unfiltered space is in direct fluid communication with the inlet;
     an outlet located at a bottom of the body, and connected to the lower portion, wherein the inlet is connected to the upper portion;
     a collection portion formed such that the unfiltered space communicates with an outside of the body, so that components remaining in the unfiltered space are accessible from the outside of the body; and
     an opening/closing element configured to open or close an outer end of the collection portion,
   wherein the membrane filter is configured such that water and components smaller than a predetermined particle diameter are removed from plasma in the unfiltered space and pass through the membrane to the filtered space, and wherein the high-concentration plasma containing components which are larger than the predetermined particle diameter remains in the unfiltered space.

* * * * *